United States Patent [19]

Young

[11] Patent Number: 4,883,654
[45] Date of Patent: Nov. 28, 1989

[54] COSMETIC PREPARATION

[76] Inventor: Deborah A. Young, 20 Panama Court, Keswick, Ontario, Canada, L4P 3L7

[21] Appl. No.: 254,152

[22] Filed: Oct. 6, 1988

Related U.S. Application Data

[63] Continuation of Ser. No. 1,853, Jan. 9, 1987.

[51] Int. Cl.$^4$ .............................................. A61K 11/56
[52] U.S. Cl. ........................................ 424/69; 424/73
[58] Field of Search ........................ 514/817, 848, 887; 424/73, 69

[56] References Cited

U.S. PATENT DOCUMENTS

| | | | |
|---|---|---|---|
| 2,257,106 | 9/1921 | Christiansen | 424/73 X |
| 2,987,446 | 6/1961 | Riethmuller | 424/73 X |
| 3,664,346 | 5/1972 | Dunn. | |
| 3,912,665 | 10/1975 | Spitzer et al. | 521/98 |
| 3,912,666 | 10/1975 | Spitzer et al. | 521/132 X |
| 3,912,667 | 10/1975 | Spitzer et al. | 521/88 X |
| 4,032,629 | 6/1977 | Osbergaus | 424/73 X |
| 4,328,319 | 5/1982 | Osipow et al. | 521/79 X |
| 4,331,653 | 5/1982 | Brown et al. | |
| 4,344,930 | 8/1982 | MacRae et al. | 424/73 X |
| 4,346,086 | 8/1982 | Sattler et al. | 514/887 X |
| 4,353,896 | 10/1982 | Levy | 514/164 X |
| 4,416,873 | 11/1983 | Puchalski et al. | 424/73 X |
| 4,422,877 | 12/1983 | Spitzer et al. | 521/79 X |
| 4,478,853 | 10/1984 | Chaussee | 424/73 X |
| 4,540,512 | 9/1985 | Seth | 514/887 X |
| 4,593,046 | 6/1986 | Gruber | 514/887 X |
| 4,608,392 | 8/1986 | Jacquet et al. | 424/73 X |
| 4,772,470 | 9/1988 | Inoue et al. | 424/81 X |

*Primary Examiner*—Nancy A. Swisher
*Attorney, Agent, or Firm*—Donald E. Hewson

[57] ABSTRACT

A toiletry formulation is provided for cosmetic use, in the form of a stable, spreadable lotion or cream incorporating a skin adherent base possessing non-irritant characteristics compatible with mucous membranes, including emulsifying agents, a skin protectant, a mild germicide to inhibit microbial growth in the formulation, and a combination of desensitizing agents for application to selected areas of the skin of a user, prior to mechanical hair depilation, such as plucking of the eyebrows, in order to minimize reaction of the skin and the local generation of pain in the plucking process.

12 Claims, No Drawings

COSMETIC PREPARATION

This is a continuing application of Ser. No. 07/001,853 filed Jan. 9, 1987 now abandoned.

BACKGROUND OF THE INVENTION

This invention is directed to a cosmetic preparation, and in particular to a lotion or cream for application to the skin of a user to desensitize the skin and mask local irritation thereof.

In the personal care aspect of toiletry preparations, little, if any, attention has been paid to facilitating grooming procedures, such as mechanical depilation, including eyebrow plucking.

It is an acknowledged fact that pain perception and pain thresholds vary widely from culture to culture, and between individuals. Factors such as motivation are significant, and the fact of whether a hurt is self-inflicted or brought about by a third party all affect the perception of pain. However, despite the range of variation in pain perception, it is known that repeated acts having a small pain quotient for each act, with continuing repetition, produce sensitization to the point that further continuance of the act become very trying. Thus, in the case of a sensitive person having a low pain threshold, who is performing depilation by plucking their eyebrows, the sensitization that takes place as each hair is drawn or plucked can be such that completion of the operation becomes trying and perhaps even impossible.

In accordance with the present invention there is provided a cosmetic preparation for local application, in an anticipatory sense to offset and mask skin irritation and local pain induced by a voluntary grooming procedure such as mechanical depilation, including eyebrow plucking.

In addition to locally offsetting the effects of pain, the subject formulation creates a local change of circulation in the skin of the subject, at the area of application, to generate a localized sensation that can detract from the instantaneous pain sensation resulting from plucking individual hairs.

The prior art is apparently quite silent in respect of formulations which have a skin desensitizing function, or it fails to express any concern as to the prospective pain that may be produced during eyebrow plucking. For example, DUNN, U.S. Pat. No. 3,664,346, issued May 23, 1972, provides a pair of eyebrow tweezers whose sole function is to be usable by persons wearing eyeglasses while at the same time plucking their eyebrows. The patent recognizes that persons having poor eyesight but desiring to pluck their eyebrows had hitherto encountered difficulties, which were said to be overcome by the geometry of the tweezer being provided. However, the patent is entirely silent as to the question of pain that may be created as the individual hairs to be plucked from the eyebrows are physically removed.

BROWN et al, in U.S. Pat. No. 4,331,653, issued May 25, 1982 provide a composition for a topical cream, which is a styptic composition that is also said to be substantially a non-sting composition. In other words, that composition has as its primary purpose that intent to stop localized bleeding without irritating the area surrounding the wound, while at the same time providing a lotion or cream having the desired non-sting but styptic characteristics. That formulation, however, does not provide a skin desensitizing effect, which effect is a desired precondition to the plucking of one's eyebrows or other mechanical depilation.

Thus, it is particularly desirable for there to be a provision of a cosmetic or toiletry formulation having a skin desensitizing effect, so as to mask local skin irritation arising from mechanical depilation. By providing a cosmetic formulation in the form of a lotion or cream, which has appreciable shelf life and which is stable during storage, the present invention places at the hands of the user an economical cosmetic preparation which can be generally obtained off-the-shelf—in much the same manner as cosmetics or toilet preparations generally.

DESCRIPTION OF THE PREFERRED EMBODIMENT

The combined base, which may be of lotion or cream formulation, includes a creamy emulsion having an appropriate viscosity range. It is non-irritating to the skin, and compatible with the mucous membranes, while at the same time demonstrating good stability during storage. Included in the base are non-ionic emulsifying agents that are relatively unaffected by additives and electrolytes, and an oily component of sufficient film strength to afford a degree of skin protection. A combination of aromatic oils provides a predetermined degree of local circulation stimulation, plus a limited degree of sensitivity suppression, as a mild analgesic. The combination is completed by the provision of a minor percentage of a mild germicide, primarily for the purpose of inhibiting microbial growth within the formulation.

It is important, in the field of toiletry formulation, to avoid preparations that produce an undue amount of sting when slight abrasions are encountered. By the intended nature of its use, the subject formulation is unlikely to come into direct contact with clothing, so that non-greasiness is not an imperative quality.

Also to be avoided is the sensation of burning, which may be produced by too high a concentration of an active ingredient.

It is desireable also to control the viscosity of the formulation so that it spreads quite readily, but is not so thin as to run.

The present invention provides a novel skin masking formulation comprising a skin non-irritating emulsion having good skin adherence and demonstrating good shelf stability, an oily component having a predetermined film strength for good skin adherence, in use, and a combination of aromatic oils to provide a predetermined degree of local dermal stimulating and sensitivity suppression, together with a mold germicide for inhibiting microbial growth within the formulation.

Thus, there is provided a toiletry formulation for cosmetic use in masking local skin irritation, the formulation incorporating a desensitizing agent within a stable, spreadable lotion or cream comprising the general formula, expressed by weight percent:

| | |
|---|---|
| Cutina CBS | about 10% |
| Emulgin B1 | about 1½% |
| Emulgin B2 | about 1½% |
| Cetiol SN | about 10% |
| menthol | in the range 0.4 to 0.8% |
| eugenol | in the range 0.5 to 2% |
| glycerin | about 5% |
| germicide | to an effective amount |

|         | -continued |
|---------|------------|
| water   | in the order of about 1%. balance to 100% |

The combined weight of menthol and eugenol is generally in the range of 1.3 to 1.6%; preferably in the range of 1.3 to 1.4%.

The preferred germicide is Germaben II, in the percentage by weight, of about ½ to 1%.

In the preferred embodiment, the menthol comprises about 0.8% by weight of the formulation; and eugenol is in the range of about 0.5 to 0.8% by weight.

The provision of a perfuming agent to mask the typical menthol and eugenol smell is contemplated; and is particularly facilitated by the easy compatibility of Cutina CBS to perfume.

The following basic compositions, pertaining to the designated components set forth above, facilitate procurement of the components and assure ease of preparation:

Cutina TM CBS (Henkel) is a blend of mono/diglycerides; fatty alcohols, triglycindis, wax esters including glyceryl stearate, cetylaryl alcohol, cetyl palmitate and glyceryl trioleate.

Generally Cutina CBS is used as a consistency factor for oil in water emulsions. It is odourless, and thus it is easily perfumed. Cutina CBS is stated to be non-irritant to the skin, as well as being compatible with the mucous membranes. It affords creamy emulsions, and therefore in an appropriate viscosity range it can add stability on storage.

Emulgin TM B1 (Henkel) is cetyl stearyl alcohol with approximately 12 mole ethylene oxide. Its CTFA (Cosmetic Toiletry and Fragrance Association) designation is Ceteareth-12. This component is a non-ionic oil in water emulsifying agent.

Emulgin TM B2 (Henkel) is cetyl stearyl alcohol with approximately 20 mole ethylene oxide. Its CTFA designation is Ceteareth-20. This component is a non-ionic oil in water emulsifier.

It should be noted that, in combination, Emulgin B1 and B2 are very effective emulsifiers. They tend to be relatively unaffected by additives and electrolytes in the formulation where they are employed.

Cetiol TM SN is an ester of a branched fatty acid, together with saturated fatty alcohols $C_{16}$-$C_{18}$. The CTFA designation is Cetearyl Alcohol Isonomanoate. It is included in the formulation as an oil component, whose purpose is as a skin protecting agent.

Germaben II (Sutton Laboratories) is a concentrated solution of Germall TM II (Diazolidinyl urea), Methylparabenzene, propylparabenzene, and propylbene glycol in the ratio 30:11:3:56 by weight. Used in the range of 0.5–1.0% by weight; it is stated to be effective for the purpose of inhibiting microbial growth in emulsions. The glycetin, menthol and eugenol are all USP purity products, available from a variety of suppliers.

Preparation of the formulations according to this invention is generally as follows:

First, the oily ingredients—Cutina CBS, Emulgin B1 and B2, Cetiol SN, and menthol, are combined and heated to about 70° to 75° C. so as to melt the mixture. The glycerin and water components are also separately combined, and also heated to about 75° C. They are then added to the first, oily ingredient mixture, while being constantly stirred. Then, the combined ingredients are cooled in a water bath, while being continually stirred, until it reaches about 40° to 45° C. At that stage, the eugenol and preservative are weighed into the mixture; after which, stirring and cooling is continued until the mixture reaches about 23° to 25° C.

There has been described a cosmetic formulation for use in desentizing the skin. Its particular purpose is as a cosmetic application when such tasks as eyebrow plucking are to be undertaken. The formulation may vary to a greater or lesser extent from that described above, without departing from the spirit and scope of the appended claims.

What is claimed is:

1. A toiletry formulation for cosmetic use in masking local skin irritation in the eye brow area arising from mechanical depilation;
   said formulation incorporating desensitizing agent in a cosmetically acceptable, stable, spreadable lotion or cream;
   the desensitizing agent comprising in the range of from 0.4 to 0.8% of menthol, and in the range of from 0.5 to 2.0% or eugenol, based on the weight of the formulation.

2. A toiletry formulation as claimed in claim 1 in which the menthol comprises 0.8% of the formulation.

3. A toiletry formulation as claimed in claim 1 in which the eugenol is in the range of about 0.5 to 0.8% by weight of the formulation.

4. A toiletry formuation as claimed in claim 1 in which the combined weight of menthol and eugenol is generally in the range of from 1.3 to 1.6% by weight of the formulation.

5. A toiletry formulation as claimed in claim 1 in which the combined weight of menthol and eugenol is generally in the range of from 1.3 to 1.4% by weight of the formulation.

6. A toiletry formulation as claimed in claim 1 comprising the general formula, expressed by weight percent:
   about 10% of a blend of mono/diglycerides; fatty alcohols, triglycerides, wax esters including glyceryl stearate, cetylaryl alcohol, cetyl palmitate and glyceryl trioleate:
   about 1.5% of cetyl stearyl alcohol with approximately 12 mole ethylene oxide;
   about 1.5% of cetyl stearyl alcohol with approximately 20 mole ethylene oxide:
   about 10% of an ester of a branched fatty acid, together with saturated fatty $C_{16}$-$C_{18}$ alcohols;
   in the range of from 0.4% to 0.8% of menthol;
   in the range of 0.5 to 2% of eugenol;
   about 5% glycerin; and
   about 0.5 to 1% diazolidinyl urea, p-methylbenzene, p-propylbenzene, and propylene glycol, in the ratio 30:11:56 by weight;
   balance to 100% of water.

7. A method for masking local skin irritation arising from mechanical depilation in the eyebrow area, comprising applying to that area a toiletry formulation
   said formulation incorporating a desensitizing agent in a cosmetically acceptable, stable, speadable lotion or cream;
   the desensitizing agent comprising in the range of from 0.4 to 0.8% of menthol, and in the range of from 0.5 to 3.0% of eugenol, based on the weight of the formulation.

8. A method is claimed in claim 7 in which the eugenol is in the range of about 0.8% by weight of the formulation.

9. A method is claimed in claim 7 in which the eugenol is in the range of about 0.5 to 0.8% by weight of the formulation.

10. A method as claimed in claim 7 in which the combined weight of menthol and eugenol is generally in the range of from 1.3 to 1.6% by weight of the formulation.

11. A method as claimed in claim 7 in which the combined weight of menthol and eugenol is generally in the range of from 1.3 to 1.4% by weight of the formulation.

12. A method as claimed in claim 7 in which the formulation comprises the general formula, expressed by weight percent;

about 10% of a blend of mono/diglycerides; fatty alcohols, triglycerides, wax esters including glyceryl stearate, cetylaryl alcohol, cetyl palmitate and glyceryl trioleate;

about 1.5% of cetyl stearyl alcohol with approximately 12 mole ethylene oxide; about 1.5% of cetyl stearyl alcohol with approximately 20 mole ethylene oxide;

about 10% of an ester of a branched fatty acid, together with saturated fatty $C_{16}$–$C_{18}$ alcohols;

in the range from 0.4% to 0.8% of menthol;

in the range 0.5 to 2% of eugenol;

about 5% glycerin; and about 0.5 to 1% diazolidinyl urea, p-methylbenzene, p-propylbenzene, and propylene glycol, in the ratio 30:11:56 by weight;

balance to 100% of water.

* * * * *